(12) United States Patent
Tokumoto

(10) Patent No.: US 6,724,005 B2
(45) Date of Patent: Apr. 20, 2004

(54) SUBSTRATE DEFECT INSPECTION METHOD AND SUBSTRATE DEFECT INSPECTION SYSTEM

(75) Inventor: Toshifumi Tokumoto, Narita (JP)

(73) Assignee: Applied Materials, Inc., Santa Clara ( * ) Notice: Subject to any disclaimer, the term of this patent is extended or adjusted under 35 U.S.C. 154(b) by 39 days.

(21) Appl. No.: 09/982,339

(22) Filed: Oct. 17, 2001

(65) Prior Publication Data

US 2002/0047098 A1 Apr. 25, 2002

(30) Foreign Application Priority Data

Oct. 18, 2000 (JP) ...................................... P2000-318047

(51) Int. Cl.[7] .............................................. G01N 21/88
(52) U.S. Cl. .............................. 250/559.4; 250/559.41; 250/559.44; 250/559.45; 356/237.2; 356/237.3
(58) Field of Search ........................ 250/559.4, 559.41, 250/559.42, 559.43, 559.44, 559.46, 559.45; 324/758, 750, 751, 752; 356/400, 237.5, 239.2, 239.3, 239.4, 239.6

(56) References Cited

U.S. PATENT DOCUMENTS 6,476,388 B1 * 11/2002 Nakagaki et al. ........... 250/310

* cited by examiner

*Primary Examiner*—David V. Bruce
*Assistant Examiner*—Hoon Song
(74) *Attorney, Agent, or Firm*—Moser Patterson & Sheridan

(57) ABSTRACT

When performing a defect inspection of a wafer W, defect observation equipment 3 first inputs defect position data from defect detection equipment 2. After a plurality of measurement points are set, the amount of position shift between the detection coordinate system and the observation coordinate system is measured for each measurement point. Then, the defect observation equipment 3 creates a first-order defect position correction formula in order to make reasonable the defect position in the detection coordinate system, based on the position shift amounts of the measurement points. This first-order defect position correction formula has three terms, for the offset component, the magnification component, and the rotation component of the observation coordinate system with respect to the detection coordinate system. Next, using the defect position correction formula, a defect position detected by the defect detection equipment 2 is corrected. By this means, the resolution of the defect observation equipment is raised, and the precision of substrate defect inspection is improved.

12 Claims, 3 Drawing Sheets

SUBSTRATE DEFECT INSPECTION METHOD AND SUBSTRATE DEFECT INSPECTION SYSTEM

BACKGROUND OF THE INVENTION

1. Field of the Invention

This invention relates to a substrate defect inspection method and substrate defect inspection system, which use defect inspection equipment and defect observation equipment to inspect defects on substrates.

2. Description of the Related Art

As devices have become finer-structured in recent years, substrate defect inspections have been performed using defect observation equipment having a scanning electron microscope (SEM). In such a defect inspection system, for example, substrate defect positions are first detected by defect detection equipment, these defect locations are observed in detail by SEM, and defects are classified. By using such defect detection equipment and defect observation equipment, substrate defect inspection can be performed without taking much time.

SUMMARY OF THE INVENTION

However, in the conventional art, adequate resolution could not be obtained from defect observation equipment, and as a result, there was the possibility of reduced precision in substrate defect inspection.

An object of this invention is to provide a substrate defect inspection method and substrate defect inspection system capable of increasing the precision of substrate defect inspection, by raising the resolution of the defect observation equipment.

As a consequence of earnest studies conducted over time, the authors have discovered that when performing substrate defect inspections using defect detection equipment and defect observation equipment, the size of the field of view (FOV) of the scanning electron microscope of the defect observation equipment cannot be made small due to a shift in the coordinate systems of the two pieces of equipment, and because of this it is difficult to raise the resolution of the defect observation equipment. Upon conducting further earnest investigations, this invention was completed, based on the finding that the shift in the coordinate systems of the two pieces of equipment has, in addition to an offset component, a magnification component and a rotation component.

That is, the substrate defect inspection method of a first concept of this invention is characterized in having a step in which a substrate defect position is detected by defect detection equipment, and information containing this defect position is sent to defect observation equipment; a step in which a plurality of measurement points on the substrate are set, and the amounts of positioning shift of each of the measurement points between the coordinate system of the defect detection equipment and the coordinate system of the defect observation equipment are measured; a step in which a defect position correction formula is created having terms for an offset component and a magnification component for the coordinate system of the defect observation equipment with respect to the coordinate system of the defect detection equipment, based on the amount of position shift for each of the measurement points; a step in which the defect position detected by the defect detection equipment is corrected using the defect position correction formula; and, a step in which an image of the corrected defect position is generated by the scanning electron microscope of the defect observation equipment, and the defect is inspected based on this image data.

By correcting defect positions detected by the defect detection equipment, using a defect position correction formula having terms for an offset component and a magnification component for the coordinate system of the defect observation equipment with respect to the coordinate system of the defect detection equipment, scattering in the shift between the corrected defect position and the actual defect position for a plurality of defects existing on the substrate can be reduced. As a result, even if the FOV size of the scanning electron microscope is reduced, and the pixel size is made smaller, a defect will be within the FOV during observation of the defect on the substrate. Hence sufficient resolution can be obtained in the defect observation equipment, and the precision of substrate defect inspection can be improved without reducing the throughput of the defect observation equipment.

It is preferred that, in the step in which the amount of position shift of each of the measurement points is measured, at least six measurement points be set on the substrate, and that, in the step in which the defect position correction formula is created, if the defect position in the x-axis direction is X and the defect position in the y-axis direction is Y in the coordinate system of the defect detection equipment, and if, in the coordinate system of the defect observation equipment with respect to the coordinate system of the defect detection equipment, the x-axis direction offset component constant is a, the x-axis direction magnification component coefficient is b, the x-axis direction rotation component coefficient is c, the y-axis direction offset component constant is d, the y-axis direction magnification component coefficient is e, the y-axis direction rotation component coefficient is f, the amount of position correction in the x-axis direction is dX, and the amount of position correction in the y-axis direction is dY, then using as the defect position correction formula $dX=a+b*X-c*Y$, $dY=d+e*Y+f*X$, the constants a through f are calculated. When using such a defect position correction formula to correct defect positions, the scattering in the shift between the corrected defect position and the actual defect position for a plurality of defects will become smaller, and so the FOV size of the scanning electron microscope can be made still smaller.

The substrate defect inspection method of a second concept of this invention is characterized in having a step in which a substrate defect position is detected by defect detection equipment, and information containing this defect position is sent to defect observation equipment; a step in which a plurality of measurement points on the substrate are set, and the amounts of shift in the positions of each measurement point between the coordinate system of the defect detection equipment and the coordinate system of the defect observation equipment are measured; a step in which a defect position correction formula is created which has terms for the offset component and the rotation component of the coordinate system of the defect observation equipment with respect to the coordinate system of the defect detection equipment, based on the amounts of shifts in position for each measurement point; a step in which the defect position detected by the defect detection equipment is corrected using the defect position correction formula; and, a step in which an image of the corrected defect position is generated by the scanning electron microscope of the defect observation equipment, and the defect is inspected based on this image data.

By correcting defect positions detected by the defect detection equipment, using a defect position correction formula having terms for an offset component and a rotation component for the coordinate system of the defect observation equipment with respect to the coordinate system of the defect detection equipment, scattering in the shift between the corrected defect position and the actual defect position for a plurality of defects existing on the substrate can be reduced. As a result, even if the FOV size of the scanning electron microscope is reduced, and the pixel size is made smaller, a defect will be within the FOV during observation of the defect on the substrate. Hence sufficient resolution can be obtained in the defect observation equipment, and the precision of substrate defect inspection can be improved without reducing the throughput of the defect observation equipment.

It is preferred that, in the step in which the amount of position shift of each of the measurement points is measured, at least six measurement points be set on the substrate, and that, in the step in which the defect position correction formula is created, if the defect position in the x-axis direction is X and the defect position in the y-axis direction is Y in the coordinate system of the defect detection equipment, and if, in the coordinate system of the defect observation equipment with respect to the coordinate system of the defect detection equipment, the x-axis direction offset component constant is a, the x-axis direction magnification component coefficient is b, the x-axis direction rotation component coefficient is c, the y-axis direction offset component constant is d, the y-axis direction magnification component coefficient is e, the y-axis direction rotation component coefficient is f, the amount of position correction in the x-axis direction is dX, and the amount of position correction in the y-axis direction is dY, then using as the defect position correction formula $dX=a+b*X-c*Y$, $dY=d+e*Y+f*X$, the constants a through f are calculated. When using such a defect position correction formula to correct defect positions, the scattering in the shift between the corrected defect position and the actual defect position for a plurality of defects will become smaller, and so the FOV size of the scanning electron microscope can be made still smaller.

The substrate defect inspection system of the first concept of this invention is a substrate defect inspection system comprising defect detection equipment, which detects substrate defect positions, and defect observation equipment, which uses a scanning electron microscope to observe defects detected by the defect detection equipment and performs defect inspections, and which is characterized in that the defect observation equipment has position shift measurement means, which sets a plurality of measurement points on the substrate, and which measures the amounts of shift in position of each of the measurement points between the coordinate system of the defect detection equipment and the coordinate system of the defect observation equipment; correction formula creation means, which creates a defect position correction formula having terms for the offset component and the magnification component of the coordinate system of the defect observation equipment with respect to the coordinate system of the defect detection equipment, based on the amounts of shift in position for each measurement point; position correction means, which uses the defect position correction formula to correct the defect position detected by the defect detection equipment; and, means to generate an image of the corrected defect position using a scanning electron microscope, and to inspect the defect based on this image data.

Thus by providing position shift measurement means, correction formula creation means and position correction means, a substrate defect inspection method of the above-described first concept can be executed, and as a result the resolution of the defect observation equipment can be raised, and the defect inspection precision can be improved.

It is preferred that the position shift measurement means sets at least six measurement points on the substrate and measures the position shift amount for each point, and that, if the defect position in the x-axis direction is X and the defect position in the y-axis direction is Y in the coordinate system of the defect detection equipment, and if, in the coordinate system of the defect observation equipment with respect to the coordinate system of the defect detection equipment, the x-axis direction offset component constant is a, the magnification component coefficient is b, the rotation component coefficient is c, the y-axis direction offset component constant is d, the magnification component coefficient is e, the rotation component coefficient is f, the amount of position correction in the x-axis direction is dX, and the amount of position correction in the y-axis direction is dY, then using as the defect position correction formula $dX=a+b*X-c*Y$, $dY=d+e*Y+f*X$, the correction formula creation means calculates the constants a through f. When using such a defect position correction formula to correct defect positions, the scattering in the shift between the corrected defect position and the actual defect position for a plurality of defects will become smaller, and so the FOV size of the scanning electron microscope can be made still smaller.

It is preferred that the defect detection equipment has defect position precision equivalent to that of the defect observation equipment.

It is preferred that the defect detection equipment have image pickup means for image pickup of the substrate, and means for extraction of substrate defect positions based on substrate image pickup data.

The substrate defect inspection system of the second concept of this invention is a substrate defect inspection system comprising defect detection equipment, which detects substrate defect positions, and defect observation equipment, which uses a scanning electron microscope to observe defects detected by the defect detection equipment and performs defect inspections, and which is characterized in that the defect observation equipment has measurement means, which sets a plurality of measurement points on the substrate, and which measures the amounts of shift in position of each of the measurement points between the coordinate system of the defect detection equipment and the coordinate system of the defect observation equipment; correction formula creation means, which creates a defect position correction formula having terms for the offset component and the rotation component of the coordinate system of the defect observation equipment with respect to the coordinate system of the defect detection equipment, based on the amounts of shift in position for each measurement point; position correction means, which uses the defect position correction formula to correct the defect position detected by the defect detection equipment; and, means to generate an image of the corrected defect position using a scanning electron microscope, and to inspect the defect based on this image data.

Thus by providing position shift measurement means, correction formula creation means and position correction means, a substrate defect inspection method of the above-described second concept can be executed, and as a result the resolution of the defect observation equipment can be raised, and the defect inspection precision can be improved.

It is preferred that the position shift measurement means sets at least six measurement points on the substrate and measures the position shift amount for each point, and that, if the defect position in the x-axis direction is X and the defect position in the y-axis direction is Y in the coordinate system of the defect detection equipment, and if, in the coordinate system of the defect observation equipment with respect to the coordinate system of the defect detection equipment, the x-axis direction offset component constant is a, the magnification component coefficient is b, the rotation component coefficient is c, the y-axis direction offset component constant is d, the magnification component coefficient is e, the rotation component coefficient is f, the amount of position correction in the x-axis direction is dX, and the amount of position correction in the y-axis direction is dY, then using as the defect position correction formula $dX=a+b*X-c*Y$, $dY=d+e*Y+f*X$, the correction formula creation means calculates the constants a through f. When using such a defect position correction formula to correct defect positions, the scattering in the shift between the corrected defect position and the actual defect position for a plurality of defects will become smaller, and so the FOV size of the scanning electron microscope can be made still smaller.

It is preferred that the defect detection equipment has defect position precision equivalent to that of the defect observation equipment.

It is preferred that the defect detection equipment have image pickup means for image pickup of the substrate, and means for extraction of substrate defect positions based on substrate image pickup data.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
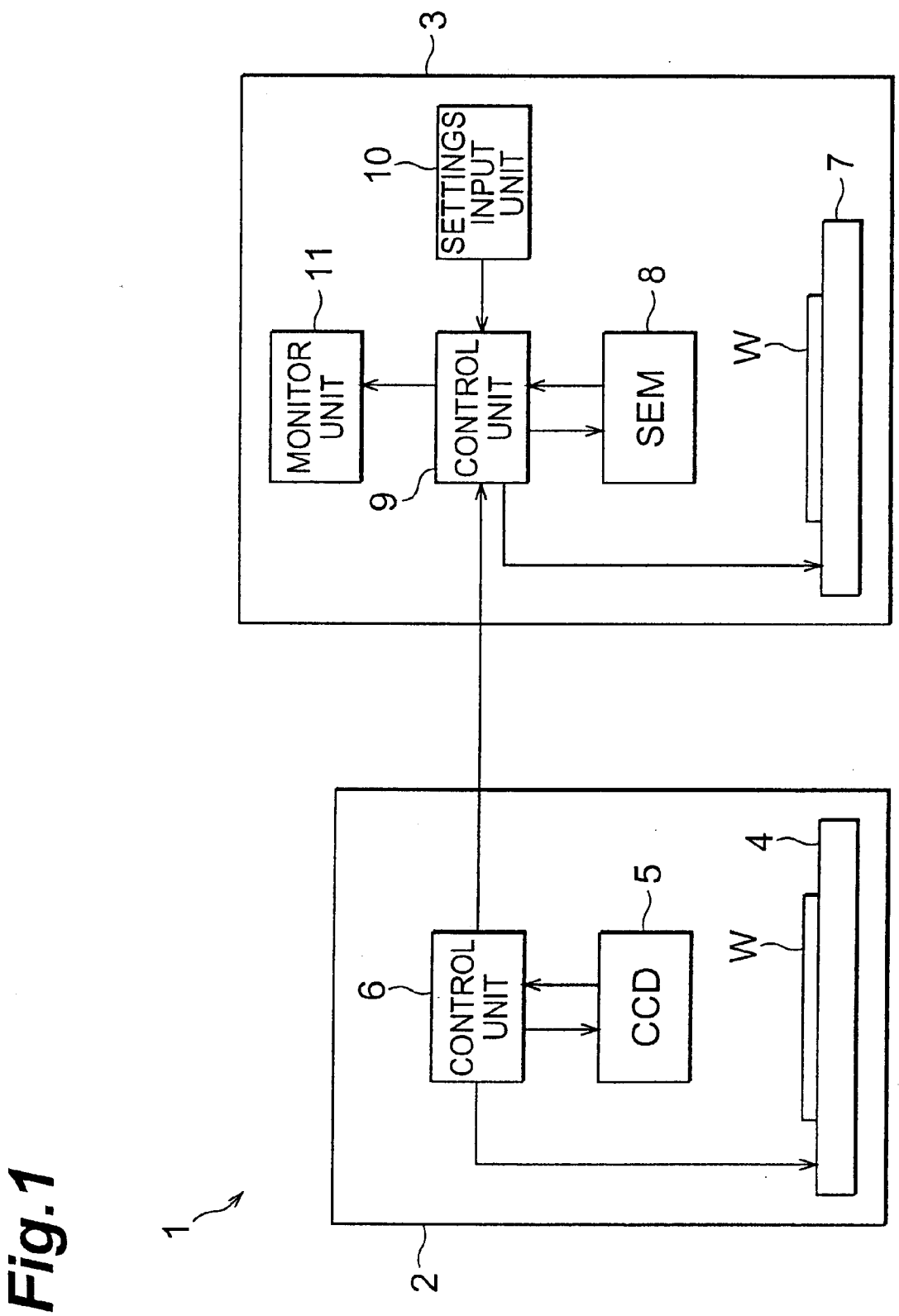
FIG. 1 is a schematic diagram showing in summary the substrate defect inspection system of one aspect of this invention.

Below, a preferred aspect of a substrate defect inspection method and substrate defect inspection system of this invention is explained, referring to the drawings.

FIG. 1 is a schematic diagram showing in summary the substrate defect inspection system of one aspect of this invention. In the figure, the defect inspection system 1 of this aspect has defect detection equipment 2 which defects defect positions on a wafer W which is a semiconductor substrate, and defect observation equipment 3 which observes defects detected by this defect detection equipment 2, and performs defect inspections.

The defect detection equipment 2 has an XY stage 4 which supports the wafer W, and a CCD camera 5 is positioned above this XY stage 4. This CCD camera 5 picks up images of the surface of the wafer W placed on the XY stage 4, and generates the image (the CCD image). The XY stage 4 and CCD camera 5 operate according to signals from the control unit 6.

Based on a CCD image from the CCD camera 5, the control unit 6 extracts the defect position existing on the wafer W, and sends the defect position data to the defect observation equipment 3 as a coordinate position (x,y) in stage coordinates. Here the control unit 6 sets the center of the wafer W as the origin of the xy coordinates, and also sets the base of the notch, or the center of the orientation flat, of the wafer as, for example, positioned on the y-axis of the xy coordinates. Also, the control unit 6 sends to the defect observation equipment 3 the chip layout and size on the wafer W, the distance from the center of the wafer W to a chip, and other data, in addition to the defect coordinate position.

It is preferred that this defect detection equipment 2 have a defect position reproducibility precision (defect position precision) of for example approximately ±3 µm. If the equipment has such a position reproducibility precision, instead of the above CCD type, laser type equipment may be used.

The defect observation equipment 3 which receives various data from the above defect detection equipment 2 has an XY stage 7 which supports the wafer W, and a scanning electron microscope (SEM) 8 is positioned above this XY stage 7. This SEM 8 irradiates the wafer W with an electron beam, and by detecting the secondary electrons emitted from the surface of the wafer W as a result, generates an image of the surface of the wafer W (SEM image). The XY stage 7 and SEM 8 operate according to signals from the control unit 9.

This control unit 9 is connected to a settings input unit 10 comprising a keyboard, mouse and similar, and to a monitor unit 11. The settings input unit 10 is used to input settings for measurement points on the wafer W, and to input required data, for measurement of the amounts of shift in positions in the coordinate system of the defect observation equipment 3 with respect to positions in the coordinate system of the defect detection equipment 2. The monitor unit 11 displays defect positions on the wafer W, the results of defect inspections, and other information.

The control unit 9 inputs various data from the defect detection equipment 3 and measurement point data set by the settings input unit 10, performs calculations to correct defect position shifts arising from shifts in the stage coordinates of the defect detection equipment 2 and the defect observation equipment 3, and also performs inspection processing of a defect on the wafer W based on a SEM image from the SEM 8.

As the defect observation equipment 3, equipment is used which has a defect position precision equivalent to that of the defect detection equipment 2, that is, a defect position precision of approximately ±3 µm.

Figure 2:
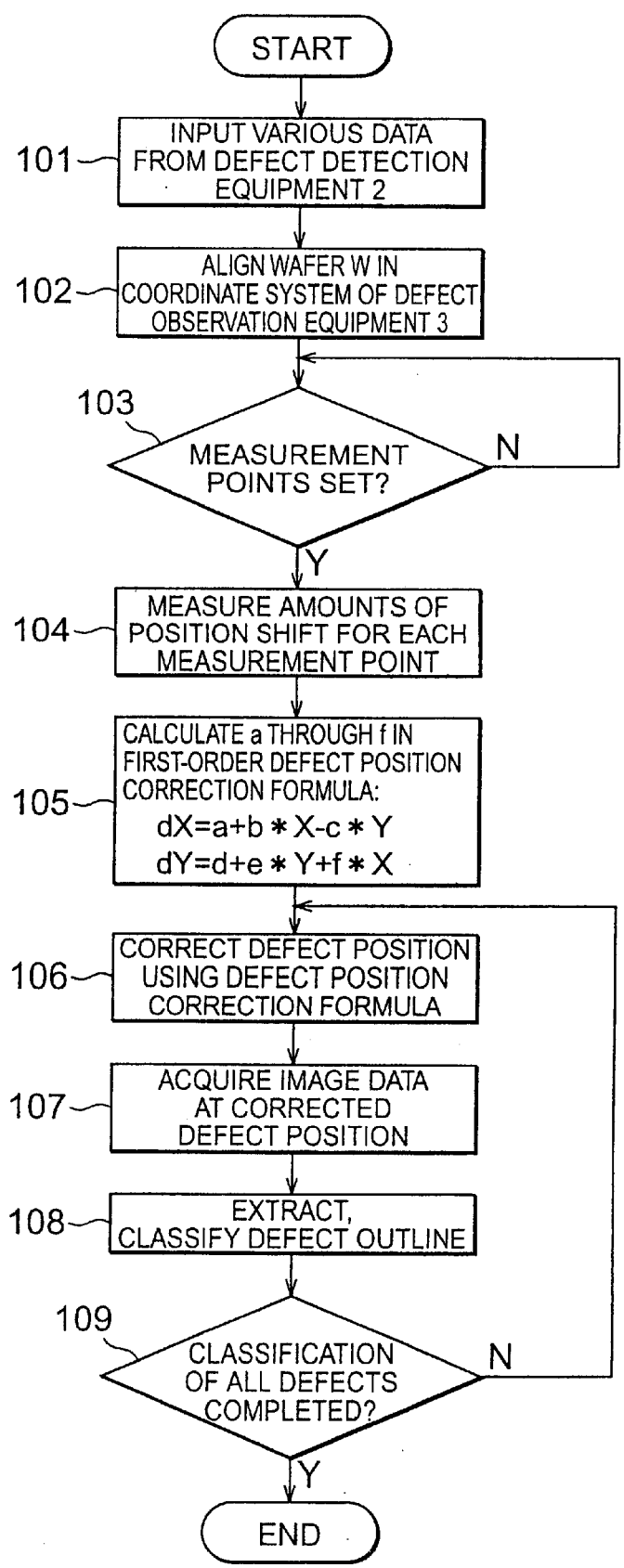
FIG. 2 is a flowchart showing the procedure of control processing by the control unit of the defect observation equipment shown in FIG. 1; and, FIG. 3 is a figure showing one example of the shifts, shown as vectors, between corrected defect positions and actual defect positions on one wafer, when defect positions are corrected by the average offset of a plurality of measurement points.

FIG. 2 is a flowchart showing the details of the procedure of control processing by the control unit 9. In the figure, first, various data, including defect position data from the control unit 6 of the defect detection equipment 2, is input (step 101). Based on this data, the alignment of the wafer W in the coordinate system of the defect observation equipment 3 is performed; specifically, the direction of the notch or the orientation flat of the wafer W is aligned with the coordinate system of the defect detection equipment 2 (step 102).

Next, a judgment is made as to whether a plurality (here, 10 or more) of measurement points for measurement of the amount of position shift have been set by the settings input unit 10 (step 103). If it is judged that the measurement points have been set, the amounts of shift in the positions between the coordinate system of the defect detection equipment 2 (hereafter called the detection coordinate system) and the coordinate system of the defect observation equipment 3 (hereafter called the observation coordinate system) for each measurement point are measured (step 104).

Here setting of the measurement points on the wafer W is performed by the operator, while viewing the image displayed by the monitor unit 11. In this case, the method for setting measurement points may be selection of a plurality of defects with characteristics existing on the wafer W; or, a plurality of measurement marks having a characteristic shape (for example, a cross shape) may be formed in advance in portions other than cells on the wafer W, and some or all of these measurement marks may be selected. When measuring the amounts of shift in the position of each measurement point, the XY stage 7 and SEM 8 are operated, moved to search for the above characteristic defects or measurement marks, and the shift amounts between the coordinate position (the coordinate position in the observation coordinate system) and the coordinate position in the detection coordinate system are measured.

Next, a first-order defect position correction formula is created in order to make reasonable the defect positions corresponding to the shift between the detection coordinate system and the observation coordinate system, based on the position shift amounts for each measurement point (step 105). The defect position correction formula is expressed as follows.

$$dX = a + b*X - c*Y \quad (1)$$

$$dY = d + e*Y + f*X \quad (2)$$

dX: Amount of position correction in the x-axis direction
dY: Amount of position correction in the y-axis direction
X: Defect position in the x-axis direction in the detection coordinate system
Y: Defect position in the y-axis direction in the detection coordinate system
a: Constant for the offset component in the x-axis direction of the observation coordinate system, with respect to the detection coordinate system
b: Constant (coefficient) for the magnification component in the x-axis direction of the observation coordinate system, with respect to the detection coordinate system
c: Constant (coefficient) for the rotation component in the x-axis direction of the observation coordinate system, with respect to the detection coordinate system
d: Constant for the offset component in the y-axis direction of the observation coordinate system, with respect to the detection coordinate system
e: Constant (coefficient) for the magnification component in the y-axis direction of the observation coordinate system, with respect to the detection coordinate system
f: Constant (coefficient) for the rotation component in the y-axis direction of the observation coordinate system, with respect to the detection coordinate system Where the rotation component of the observation coordinate system with respect to the detection coordinate system is concerned, the counterclockwise direction of rotation is taken to be positive.

In step 103, the coordinate positions (X,Y) of a plurality of measurement points are set, and in step 104, because the amounts of position correction (dX,dY) corresponding to the coordinate positions (X,Y) of each of these measurement points are obtained, by substituting these coordinate positions (X,Y) and position correction amounts (dX,dY) into the above defect position correction formula, each of the constants (a,d), (b,e), (c,f) can be calculated. If there are at least six coordinate positions (X,Y) of measurement points, the constants a through f can be calculated; however, it is preferred that as many measurement points as possible be set across the surface of the wafer W, to obtain a more reasonable first-order defect position correction formula.

Next, using the above defect position correction formula, a defect position (X,Y) detected by the defect detection equipment 2 is corrected (step 106). Correction of this defect position is performed using the following equations.

$$Xn = X + dX$$

$$Yn = Y + dY$$

Xn: Defect position in the x-axis direction in the observation coordinate system, after correction
Yn: Defect position in the y-axis direction in the observation coordinate system, after correction Next, the XY stage 7 and SEM 8 are operated, and a SEM image of the surface of the wafer W in a location including the corrected defect position (Xn,Yn) is generated (step 107). At this time, observations are performed to determine where in the field of view (FOV) of the SEM 8 the defect is initially located, and the defect portion is then enlarged for further observation.

Following this, the outline (shape) of the defect is extracted from the SEM image data, and defect classification is performed (step 108). Here defect classifications are by defect type (for example, particles, foreign matter, and so on), and by the location of the defect (for example, on the lower layer, on the upper layer, and so on). The results of inspections of defects of such patterns are then displayed by the monitor unit 11.

Next, a judgment is made as to whether all the defects on the wafer W have been classified (step 109), and if classification of all defects is not ended, processing returns to step 106, and correction of defect position, acquisition of SEM image data for the defect, and defect classification are performed in order.

In defect observation equipment 3 as described above, the settings input unit 10, the monitor unit 11 and the steps 103, 104 of the control unit 9 comprise position shift measurement means which sets a plurality of measurement points on the wafer W, and measures the position shift amount for each measurement point between the coordinate system of the defect detection equipment 2 and the coordinate system of the defect observation equipment 3. Step 105 of the control unit 9 comprises correction formula creation means, in which a defect position creation formula is created, having terms for the offset component and the magnification component or the rotation component of the coordinate system of the defect observation equipment 3 with respect to the coordinate system of the defect detection equipment 2, based on the position shift amounts of the measurement points. Step 106 of the control unit 9 comprises position correction means, in which a defect position detected by the defect detection equipment 2 is corrected using the defect position correction formula. Steps 107 and 108 of the control unit 9 comprise means to generate an image of the corrected defect position by a scanning electron microscope 8, and to inspect the defect based on the image data.

In a defect inspection system 1 configured as described above, in order to raise the defect extraction sensitivity without lowering the throughput of the defect observation equipment 3, it is effective to reduce the FOV size of the SEM 8 and make the pixel size smaller. However, because there exists a shift in the coordinate systems of the defect detection equipment 2 and the defect observation equipment 3, if the FOV size is made too small, defects may not be included within the FOV.

In order to accommodate this shift in coordinate systems occurring between the two types of equipment, defect positions detected by the defect detection equipment 2 must be corrected by the defect observation equipment 3. As the method for correction of defect positions, a plurality (for example, three) of measurement points are set on the wafer W, the average value of position shift amounts for each measurement point between the detection coordinate system and the observation coordinate system is calculated, and this average offset may be used to correct defect positions.

Figure 3:
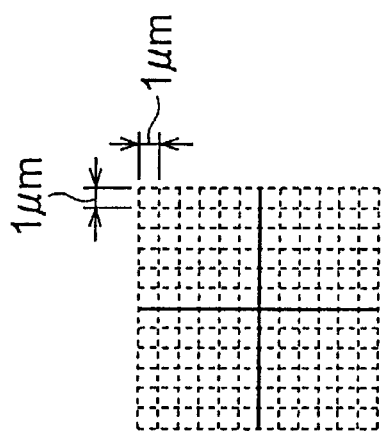
Figure 3:
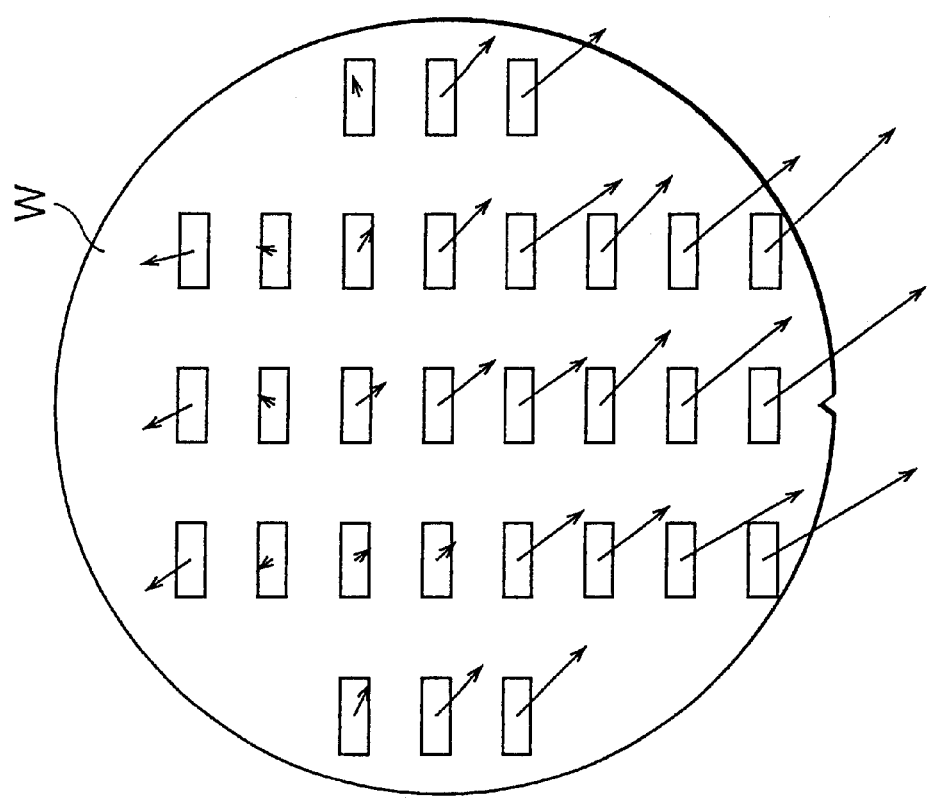

FIG. 3 shows one example of a case in which defect positions are corrected by an average offset of a plurality of measurement points; the shift between the corrected defect position and the actual defect position is shown, in vector form, for a plurality of locations on the surface of a single wafer W. In this case, the scattering (range) of shifts in defect positions in the x-axis direction is 10.05 $\mu$m, and the scattering of shifts in defect positions in the y-axis direction is 11.36 $\mu$m, so that the scattering in shifts of corrected defect positions and actual defect positions is large. Consequently, despite the fact that the defect position precision of the defect detection equipment 2 and of the defect observation equipment 3 is in both cases approximately ±3 $\mu$m, a FOV size of the SEM 8 of approximately 14 to 20 $\mu$m must be used.

On the other hand, if, as described above, a first-order defect position correction formula is created having terms for the offset component, magnification component and rotation component of the observation coordinate system with respect to the detection coordinate system, and this correction formula is used to correct defect positions detected by the defect detection equipment 2, then the scattering in shifts in the corrected defect positions and the actual defect positions on the surface of a single wafer W will be reduced. Specifically, in a simulation of measurements of position shift amounts for each measurement point on the wafer W, if in the above equations (1) and (2)

$(a,d) = (2.01\ \mu m,\ -2.06\ \mu m)$ $(b,e) = (7.39\ ppm,\ 66.3\ ppm)$ $(c,f) = (48.7\ urad,\ 0.88\ urad)$ then the scattering in shifts in defect positions in the x-axis direction becomes 2.93 $\mu$m, the scattering in shifts in defect positions in the y-axis direction becomes 2.76 $\mu$m, and there is great improvement compared with the case in which defect positions are corrected by the average offset.

In this aspect, by correcting defect positions using a first-order defect position correction formula having terms for the offset component, magnification component, and rotation component of the observation coordinate system with respect to the detection coordinate system, the scattering in shifts of corrected defect positions and actual defect positions can be reduced, so even if the FOV size of the SEM 8 is made smaller, and pixel sizes are made smaller, defects on the wafer W can be reliably included in the FOV. Hence adequate resolution can be obtained in the defect observation equipment 3, and the precision of inspection of defects on the wafer W is improved.

This invention is not limited to the above aspect. For example, in the above aspect, defect positions are corrected using a first-order defect position correction formula having terms for the offset component, magnification component, and rotation component of the observation coordinate system with respect to the detection coordinate system; but the defect position correction formula is not limited to this in particular. For example, as the defect position correction formula, a correction formula which has only terms for the offset component and the magnification component of the observation coordinate system with respect to the detection coordinate system, or a correction formula which has only terms for the offset component and the rotation component of the observation coordinate system with respect to the detection coordinate system, may be used. In this case also, the scattering in the shift of corrected defect positions and actual defect positions can be reduced compared with the case of correction of defect positions by the average offset of a plurality of measurement points.

While the foregoing is directed to embodiments of the present invention, other and further embodiments of the invention may be devised without departing from the basic scope thereof, and the scope thereof is determined by the claims that follow.

What is claimed is:

1. A substrate defect inspection method, comprising:

detecting a substrate defect position by the use of defect detection equipment, and sending information including the defect position to defect observation equipment;

setting a plurality of measurement points on said substrate, and measuring an amount of shift in position of each of said measurement points between the coordinate system of said defect detection equipment and the coordinate system of said defect observation equipment;

creating a defect position correction formula, having terms for the offset component and the magnification component of the coordinate system of said defect observation equipment with respect to the coordinate system of said defect detection equipment, based on the amount of position shift for each of said measurement points;

correcting said defect position detected by said defect detection equipment by using said defect position correction formula; and generating an image of said corrected defect position by the scanning electron microscope of said defect observation equipment, and inspecting the defect based on said image data.

2. The substrate defect inspection method according to claim 1, wherein measuring the amounts of shift in position of each of said measurement points comprises setting at least six measurement points on said substrate; and correcting said defect position by using said defect correction formula comprises using the defect position correction formulae dX=a+b*X−c*Y, dY=d+e*Y+f*X to calculate the constants a through f, wherein the defect position in the x-axis direction in the coordinate system of said defect detection equipment is X, the defect position in the y-axis direction is Y, the constant for the offset component in the x-axis direction of the coordinate system of said defect observation equipment with respect to the coordinate system of said defect detection equipment is a, the constant for the magnification component in the x-axis direction is b, the constant for the rotation component in the x-axis direction is c, the constant for the offset component in the y-axis direction is d, the constant for the magnification component in the y-axis direction is e, the constant for the rotation component in the y-axis direction is f, the position correction amount in the x-axis direction is dX, and the position correction amount in the y-axis direction is dY.

3. A substrate defect inspection method, comprising:

detecting a substrate defect position by the use of defect detection equipment, and sending information including the defect position to defect observation equipment;

setting a plurality of measurement points on said substrate, and measuring an amount of shift in position of each of said measurement points between the coordinate system of said defect detection equipment and the coordinate system of said defect observation equipment;

creating a defect position correction formula, having terms for the offset component and the rotation component of the coordinate system of said defect observation equipment with respect to the coordinate system of said defect detection equipment, based on the amount of position shift for each of said measurement points;

correcting said defect position detected by said defect detection equipment using said defect position correction formula; and generating an image of said corrected defect position by the scanning electron microscope of said defect observation equipment, and inspecting the defect based on said image data.

4. The substrate defect inspection method according to claim 3, wherein measuring the amounts of shift in position of each of said measurement points comprises setting at least six measurement points on said substrate; and, correcting said defect position by using said defect correction formula comprises using the detect position correction formulae $dX=a+b*X-c*Y$, $dY=d+e*Y+f*X$ to calculate the constants a through f, wherein the defect position in the x-axis direction in the coordinate system of said defect detection equipment is X, the defect position in the y-axis direction is Y, the constant for the offset component in the x-axis direction of the coordinate system of said defect observation equipment with respect to the coordinate system of said defect detection equipment is a, the constant for the magnification component in the x-axis direction is b, the constant for the rotation component in the x-axis direction is c, the constant for the offset component in the y-axis direction is d, the constant for the magnification component in the y-axis direction is e, the constant for the rotation component in the y-axis direction is f, the position correction amount in the x-axis direction is dX, and the position correction amount in the y-axis direction is dY.

5. A substrate defect inspection system, comprising defect detection equipment which detects substrate defect positions and defect observation equipment which observes defects detected by said defect detection equipment using a scanning electron microscope and performs defect inspections, wherein said defect observation equipment comprises:

position shift measurement means, which sets a plurality of measurement points on said substrate, and measures an amount of position shift of each of said measurement points between the coordinate system of said defect detection equipment and the coordinate system of said defect observation equipment;

correction formula creation means, which creates a defect position correction formula having terms for the offset component and the magnification component of the coordinate system of said defect observation equipment with respect to the coordinate system of said defect detection equipment, based on the amount of position shift of each of said measurement points;

position correction means, which corrects said defect position detected by said defect detection equipment, using said defect position correction formula; and means for generating an image of said corrected defect position using said scanning electron microscope, and inspecting the defect based on the image data.

6. The substrate defect inspection system according to claim 5, wherein said position shift measurement means sets at least six measurement points on said substrate, and measures an amount of position shift for each measurement point; and if the defect position in the x-axis direction in the coordinate system of said defect detection equipment is X, the defect position in the y-axis direction is Y, the constant for the offset component in the x-axis direction of the coordinate system of said defect observation equipment with respect to the coordinate system of said defect detection equipment is a, the constant for the magnification component in the x-axis direction is b, the constant for the rotation component in the x-axis direction is c, the constant for the offset component in the y-axis direction is d, the constant for the magnification component in the y-axis direction is e, the constant for the rotation component in the y-axis direction is f, the position correction amount in the x-axis direction is dX, and the position correction amount in the y-axis direction is dY, then said correction formula creation means uses $dX=a+b*X-c*Y$, $dY=d+e*Y+f*X$ as said defect position correction formula to calculate the constants a through f.

7. The substrate defect inspection system according to claim 5, wherein said defect detection equipment has a defect position precision equivalent to that of said defect observation equipment.

8. The substrate defect inspection system according to claim 5, wherein said defect detection equipment has image pickup means which performs image pickup of said substrate, and means to extract the defect position of said substrate based on image pickup data for said substrate.

9. A substrate defect inspection system, comprising defect detection equipment which detects substrate defect positions and defect observation equipment which observes defects detected by said defect detection equipment using a scanning electron microscope and performs defect inspections, wherein said defect observation equipment comprises:

position shift measurement means, which sets a plurality of measurement points on said substrate, and measures an amount of position shift of each of said measurement points between the coordinate system of said defect detection equipment and the coordinate system of said defect observation equipment;

correction formula creation means, which creates a defect position correction formula having terms for the offset component and the rotation component of the coordinate system of said defect observation equipment with respect to the coordinate system of said defect detection equipment, based on the position shift amount of each of said measurement points;

position correction means, which corrects said defect position detected by said defect detection equipment, using said defect position correction formula; and means which generates an image of said corrected defect position using said scanning electron microscope, and which inspects the defect based on the image data.

10. The substrate defect inspection system according to claim 9, wherein said position shift measurement means sets at least six measurement points on said substrate, and measures an amount of position shift for each measurement point; and if the defect position in the x-axis direction in the coordinate system of said defect detection equipment is X, the defect position in the y-axis direction is Y, the constant for the offset component in the x-axis direction of the coordinate system of said defect observation equipment with respect to the coordinate system of said defect detection equipment is a, the constant for the magnification component in the x-axis direction is b, the constant for the rotation component in the x-axis direction is c, the constant for the offset component in the y-axis direction is d, the constant for the magnification component in the y-axis direction is e, the constant for the rotation component in the y-axis direction is f, the position correction amount in the x-axis direction is dX, and the position correction amount in the y-axis direction is dY, then said correction formula creation means uses $dX=a+b*X-c*Y$, $dY=d+e*Y+f*X$ as said defect position correction formula to calculate the constants a through f.

11. The substrate defect inspection system according to claim 9, wherein said defect detection equipment has a defect position precision equivalent to that of said defect observation equipment.

12. The substrate defect inspection system according to claim 9, wherein said defect detection equipment has image pickup means which performs image pickup of said substrate, and means to extract the defect position of said substrate based on image pickup data for said substrate.

* * * * *